United States Patent

Court et al.

[11] Patent Number: 5,863,752
[45] Date of Patent: Jan. 26, 1999

[54] METHODS AND APPARATUS FOR MONITORING THE GROWTH OF MICROORGANISMS IN LIQUID CULTURE

[75] Inventors: Nigel Timothy Court; Richard Paul Hayes-Pankhurst, both of London, Great Britain; Neil Laurence Evans, Palmyra, Australia; Judith Marjorie Anderson; Roy Holbrook, both of Sharnbrook, Great Britain; Peter Richard Stephenson, Felmersham; Arthur Maurice Weightman, Bromham, both of Great Britain

[73] Assignee: Oxoid Limited, Basingstoke, England

[21] Appl. No.: 30,488

[22] PCT Filed: Jul. 20, 1992

[86] PCT No.: PCT/GB92/01327

§ 371 Date: Jun. 2, 1993

§ 102(e) Date: Jun. 2, 1993

[87] PCT Pub. No.: WO93/03178

PCT Pub. Date: Feb. 18, 1993

[30] Foreign Application Priority Data

Aug. 2, 1991 [EP] European Pat. Off. .............. 91307144

[51] Int. Cl.⁶ .............................. C12Q 1/04; C12M 1/34
[52] U.S. Cl. ................................. 435/34; 73/52; 422/64; 422/107; 435/286.1; 435/287.1; 435/287.5
[58] Field of Search ..................... 215/247, 251, 215/269, 270; 73/52, 705; 422/102, 107, 64; 435/34, 284, 289, 291, 296, 312, 286.1; 287.1, 287.5; 356/357, 358

[56] References Cited

U.S. PATENT DOCUMENTS

| | | | |
|---|---|---|---|
| 3,327,584 | 6/1967 | Kissinger | 356/375 |
| 4,117,718 | 10/1978 | Hayward | 73/52 |
| 4,152,213 | 5/1979 | Abnell | 195/103 |
| 4,158,310 | 6/1979 | Ho | 73/705 |
| 4,249,076 | 2/1981 | Bergstrom et al. | 250/227.23 |
| 4,250,266 | 2/1981 | Wade | 435/291 X |
| 4,314,029 | 2/1982 | Ohtake et al. | 435/291 |
| 4,456,138 | 6/1984 | Bereziat | 215/251 X |
| 4,547,668 | 10/1985 | Tsikos | 73/705 X |
| 4,620,093 | 10/1986 | Barkhoudarian et al. | 73/705 X |
| 4,674,642 | 6/1987 | Towns et al. | 215/270 X |
| 4,735,508 | 4/1988 | Bellio | 73/52 X |
| 4,812,408 | 3/1989 | Hammann et al. | 435/296 |
| 4,907,443 | 3/1990 | Pailler | 73/705 X |
| 4,908,951 | 3/1990 | Gurny | 33/503 |
| 4,944,922 | 7/1990 | Hayashi | 422/65 X |
| 5,088,612 | 2/1992 | Storar et al. | 215/247 |
| 5,232,839 | 8/1993 | Eden et al. | 435/296 X |

FOREIGN PATENT DOCUMENTS

| | | |
|---|---|---|
| 124193 | 11/1984 | European Pat. Off. . |
| 340902 | 11/1989 | European Pat. Off. . |
| 2457044 | 10/1976 | Germany . |

OTHER PUBLICATIONS

C.M. Stevens et al. *J. Clin Microbiol.* 1994, 32, 1750–1756.

*Primary Examiner*—Arlen Soderquist
*Attorney, Agent, or Firm*—Pillsbury Madison & Sutro LLP

[57] ABSTRACT

A method of monitoring the growth of microorganisms in liquid culture involving the detection of pressure change in a gas-tight container such as a blood culture bottle incorporating a flexible diaphragm (septum) by detecting displacement of the septum, is characterised by the position or conformation of the diaphragm being repeatedly sensed using a distance-measuring means, such as a laser, preferably capable of detecting a variation in the position or conformation of the diaphragm to an accuracy of 200μ or better, with a portion of the container adjacent the diaphragm conveniently being used as a reference to detect any relative positional or conformational change of the diaphragm. Preferably the laser repeatedly scans a plurality of containers mounted in a holder such as a flat bed or a carousel.

14 Claims, 13 Drawing Sheets

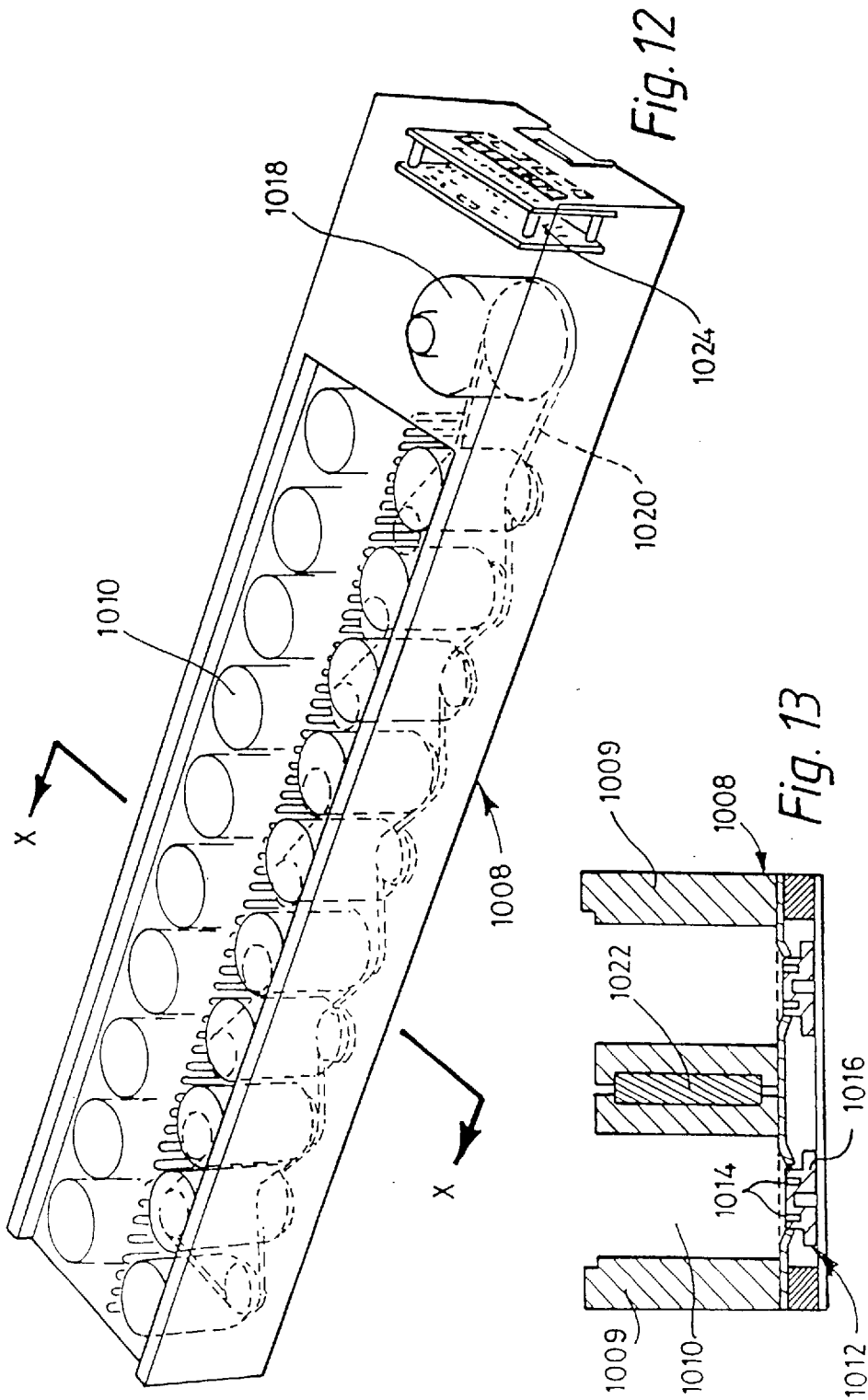

METHODS AND APPARATUS FOR MONITORING THE GROWTH OF MICROORGANISMS IN LIQUID CULTURE

FIELD OF INVENTION

This invention relates to micro-organism growth, and concerns a method and apparatus for monitoring the growth of micro-organisms, for example in blood culture bottles.

SUMMARY OF THE INVENTION

In one aspect, the invention provides a method of monitoring the growth of micro-organisms in liquid culture in a gas-tight container incorporating a flexible diaphragm capable of moving in response to pressure changes within the container, by detecting displacement of the diaphragm, wherein the position or conformation of the diaphragm is repeatedly sensed using distance-measuring means.

Preferably the distance-measuring means is capable of detecting a variation or the position or conformation of the diaphragm to an accuracy of $200\mu$ or less, more preferably $100\mu$ or less, even more preferably $50\mu$ or less, eg about $10\mu$.

The distance-measuring means is preferably a laser.

Preferably a portion or the container adjacent the diaphragm is used as a reference against which to detect any relative positional or conformational change of the diaphragm.

The distance-measuring means can desirably scan across the diaphragm, and use one or more fixed reference points associated with the diaphragm when determining any variation in the displacement of the diaphragm.

The container is conveniently constructed of rigid material, with the sole exception of the diaphragm, so that the diaphragm alone is displaced in response to pressure changes within the container. The diaphragm is conveniently made of resilient flexible plastics or rubber material.

The container preferably comprises a culture bottle, having a bottle closure incorporating a flexible diaphragm known as a septum.

In a preferred arrangement, the distance-measuring means repeatedly senses or scans a plurality of containers, as part of an automated monitoring system. The containers are conveniently arranged in an array with the array and distance-measuring means arranged for relative movement such that the containers are sequentially scanned by the distance-measuring means.

The containers can be located, for example, in a generally stationary holder such as a tray or flat bed arrangement with respect to which the distance-measuring means moves to scan the containers in turn, hit the containers being gently shaken or stirred (e.g. by use of an individual magnetic stirring device in each container) to agitate the contents during incubation.

Alternatively, the plurality of containers can be arranged in an array to be presented sequentially to the distance-measuring means which remains generally stationary. This can conveniently be achieved by mounting the containers in a carousel arrangement.

In a particularly preferred embodiment, the carousel can revolve continuously about-a horizontal axis, and the plurality of containers are arranged around the circumference of the carousel such that rotation of the carousel generates end-over-end mixing of the contents of the containers.

Where an array of containers is monitored, it is highly desirable that each container displays a unique machine-readable identifying reference, such as a bar-code.

The invention thus also provides apparatus for monitoring the growth of micro-organisms in liquid culture, comprising means for holding an array of gas-tight containers each containing a liquid test sample and each incorporating a flexible diaphragm capable of moving in response to pressure changes within the container, distance-measuring means capable of detecting changes in position or conformation of each diaphragm, means for providing relative movement between the containers and the distance-measuring means for repeatedly presenting the containers individually in turn to the distance-measuring means, and means for recording and/or displaying data obtained from the distance-measuring means.

The means for recording and/or displaying data conveniently comprises microprocessor means programmed to store at least the immediately preceding reading for each diaphragm and to record that data and/or signal to an operator of the apparatus any variation between successive positional or conformational readings of the individual diaphragms.

In one embodiment the container holding means comprises a carousel revolvable to bring each container in turn to a reading station. The carousel is preferably revolvable about a horizontal axis and the containers are mounted round the periphery of the carousel such that liquid contents of each container experience end-over-end mixing while the carousel revolves.

The carousel is preferably provided at its periphery with a plurality of holding means each capable of securely retaining a culture bottle, preferably of the conventional laboratory standard type. The holding means can, for example, be a spring clip into which the bottle can be easily inserted and from which it can be easily removed. In embodiments of the invention where the rotation of the carousel is about a horizontal axis and promotes end-over-end mixing of the contents of each bottle, the fixing means for each bottle should be capable of securly holding the bottle in place even when the bottle is inverted.

The holding means for each bottle in the array, conveniently comprises a recess or "nest", preferably moulded to correspond to the external shape of the bottle. As a further preferred desire, the bottle is crowded with an over-cover formed, for example, as a plastics moulding which can be fitted onto the neck of a conventional laboratory culture bottle. Holding means can engage either with the bottle itself or with the over-cover. The over-cover should be positively located on the neck of the bottle, eg. by being a "snap" push fit over the crimped seal of the standard bottle. Preferably the over-cover is of an irregular shape, compared to the bottle, and together with a correspondingly-shaped irregular aperture in the holding means can facilitate location of the bottle in a specific position. This is particularly useful if the over-cover or bottle carries a machine-readable identifying reference, such as a bar code, which needs to be presented to a reading means while the apparatus is in use. An ideal position for a bar code or similar reference is on a substantially flat portion of the upper surface of the over-cover.

Although the over-cover can be supplied to the user as a separate item, it is preferable for the filled sealed bottle to be supplied with the over-cover already attached. There is no need for the user to remove the over-cover. If desired, the over-cover can be provided with a removable seal protecting the diaphragm. This removable seal can, for example, be a tear-off portion of the moulding itself. In one embodiment this readily removable seal is sufficiently thin to enable a sample to be injected into the culture bottle directly through the seal and the septum beneath; this is easily, achieved if the over-cover is a plastics moulding and the sealing portion above the septum is thin. The inoculated bottle can then be transferred (if necessary) to a central culturing facility while the seal is in place, and the seal removed by the operator of the culture facility before the bottle and over-cover are placed in the apparatus. Alternatively, the top of the cover can be torn off prior to sample injection.

The means for sensing movement of the diaphragm, eg. relative to the rim of the bottle seal, can be any means capable of measuring distances accurately. Preferably, this is to an accuracy of $200\mu$ or less, more preferably $100\mu$ or less, even more preferably $50\mu$ or less, eg about $10\mu$. A variety of distance-measuring means may be used, for example lasers, fibre-optics, non-optical electromagnetic radiation, and ultrasound. Laser-based systems are preferred, and are available commercially for measuring small distances, and such equipment can be easily used in the context of the invention. Particularly suitable sensing systems include those available commercially form Matsushita, under their MQ range, using an optical triple beam semi-conductor laser sensor, such as Model LA40 having a measuring range of 30 to 50 mm and a resolution of $10\mu$, and Model LA75 having a measuring range of 50 to 100 mm and a resolution of $150\mu$, and also Nippon Model LAS 5010 from Nippon Automation Co Ltd, Japan which has a measurings range of 45 to 55 mm and a resolution of $10\mu$.

In practice, conventional rubber or plastics septa can be used without loss of sensitivity of the method, but if desired, septa that are thinner than standard can be used.

It may be useful to include a reference container in the holding means that can be monitored by the distance-measuring means to provide an indication of chances in environmental conditions within the apparatus, particularly pressure and temperature changes, so that results from other containers can be adjusted if necessary to compensate for changes due to varying environmental conditions.

Primary advantages of the invention, in preferred embodiments at least, include the following:

a) Greater sensitivity in the detection of micro-organism growth when compared to presently-available commercial systems. This enables earlier detection of the presence of micro-organisms in samples.

b) Enhanced ability to distinguish between groups of micro-organisms (eg. fermentative and non-fermentative aerobes) during early stages of the procedure.

c) The ability to use industry-standard commercially available septum-sealed bottles (if necessary fitted with an over-cover to facilitate location in an automated bottle-handling facility).

d) Enhanced sensitivity and speed of detection of micro-organism growth can be achieved using conventional around media.

The invention therefore lends itself to the use of present day standard micro-organism culture bottles and media, and does not require significant changes from conventional laboratory practice.

Embodiments of the invention will now be described, by way of illustration, in the following examples and with reference to the accompanying drawings, in which:

FIG. 12 is a schematic perspective view of part of the arrangement shown in FIG. 11, to a further enlarged scale;

FIG. 13 is a sectional view in the direction of arrows X in FIG. 12; and

DETAILED DESCRIPTION OF THE DRAWINGS

Figure 1:
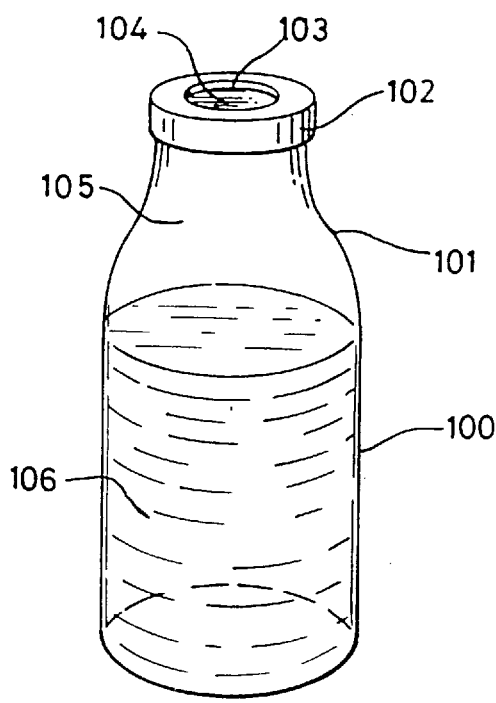
FIG. 1 is a perspective view of a culture bottle of standard configuration.

FIG. 1 shows a standard commercially available culture bottle as is widely used in laboratories and hospitals in the culturing of samples, such as blood samples, to detect the presence of micro-organisms. The culture bottle comprises a cylindrical glass bottle 100 of circular cross section with a gently tapering broad neck 101 closed by a crimped metal seal 102, typically made from aluminium. Other sealing methods, such as threaded caps, can be used. Such bottles are normally supplied to the end user in sealed form containing an appropriate liquid growth medium 106. The crimped seal has a central aperture 103 which is closed by a septum or diaphragm 104 of rubber or plastics material. A sample, such as a sample of blood or other body fluid, can be injected directly into the culture bottle through the septum by use of a syringe, and the septum seals itself when the needle of the injecting syringe is withdrawn from the bottle.

Pressure variations within the sealed bottle can cause the septum to deform inwardly or outwardly relative to the interior of the bottle, adopting a concave or convex configuration. Under normal circumstances there will always be a volume of gas in the head space 105 because the liquid growth medium 106 and injected sample will only occupy part of the bottle capacity. Changes in the internal pressure can result from temperature changes, eg. warming of the bottle to normal culturing conditions. In general, culture is conducted at elevated temperature, eg. 37° C. If micro-organisms are present in the injected sample, they will grow in the medium and many species produce gas during growth. This also increases the internal pressure and causes the septum to deform outwardly further. Other species may cause a net reduction in the gas content of the bottle, and this leads to a drop in internal pressure and the septum deforms inwardly.

Figure 2:
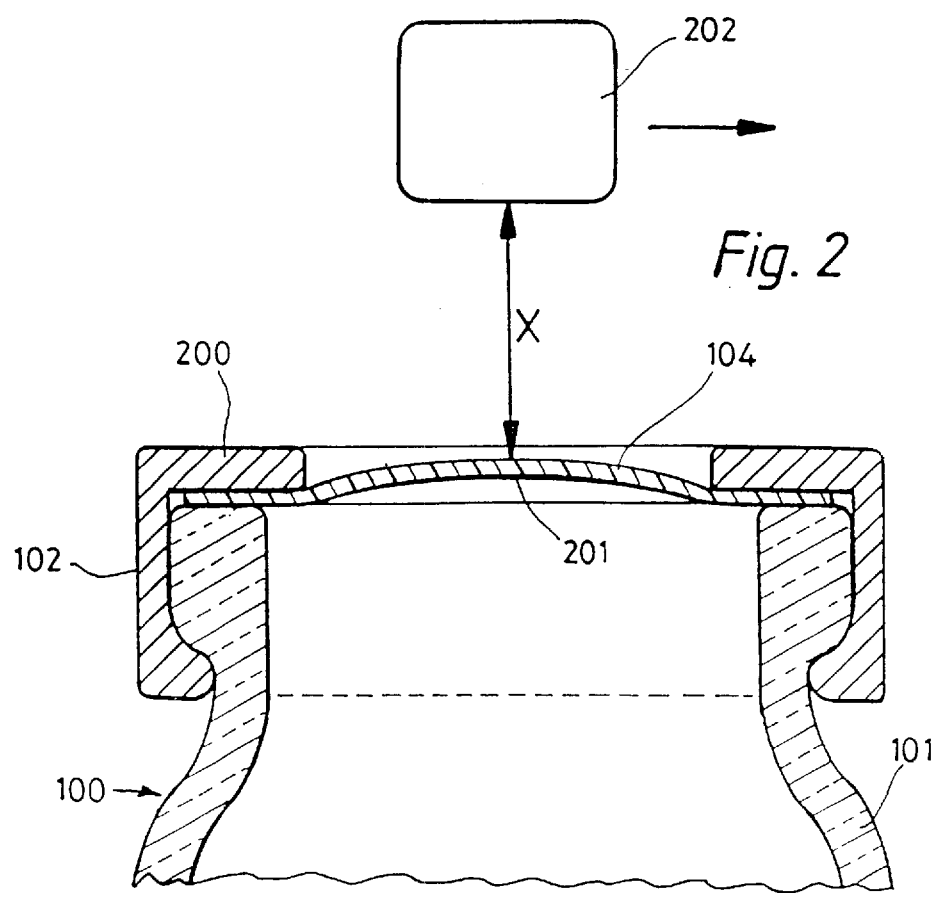
FIG. 2 is a vertical cross-section, to an enlarged scale, of the top part of the bottle shown in FIG. 1.

Referring to FIG. 2, the invention relies on the measurement of small changes in the position or profile of the septum relative, for example, to the rim 200 of the crimped bottle seal 102. The centre 201 of the septum 104 will rise if the pressure within the bottle increases. Alternatively, the septum will drop and become concave if there is a reduction in internal pressure. By employing a laser or similar sensitive distance-measuring device 202, which can scan repeatedly across the top of the bottle, the movement of the septum relative to the fixed position of the rim 200 of the seal can be monitored. The laser 202 measures distance X, between the laser and the centre 201 of the septum, and also the distance between the laser and a fixed reference point on the bottle such as the rim of the seal to provide a measure of movement of the septum. Because the rim of the seal acts as a fixed reference point relative to the septum, the precise position of the bottle at the time of measurement does not matter. The bottle can form part of an array of identical bottles with there being relative movement between the bottles and laser so that each bottle is scanned by the laser, eg. by moving the bottles in turn to a reading station associated with the laser, for example using a carousel arrangement, or by moving the laser over a fixed array of bottles. As noted above, there is no need for an individual bottle to be positioned in a precise relationship with the laser reader, because each bottle carries its own fixed internal reference (the rim of the seal). Therefore there are far fewer physical constraints on the design of the culturing/reading unit, and this offers considerable advantages over many commercially available multi-bottle culturing/recording systems.

Other reference points can be chosen such as the periphery of the septum immediately adjacent to the rim, as this part of the septum is effectively fixed.

If desired, the laser can sense the profile (curvature) of the septum, rather than simply the relative displacement of a point (such as the centre) of the septum.

Figure 3:
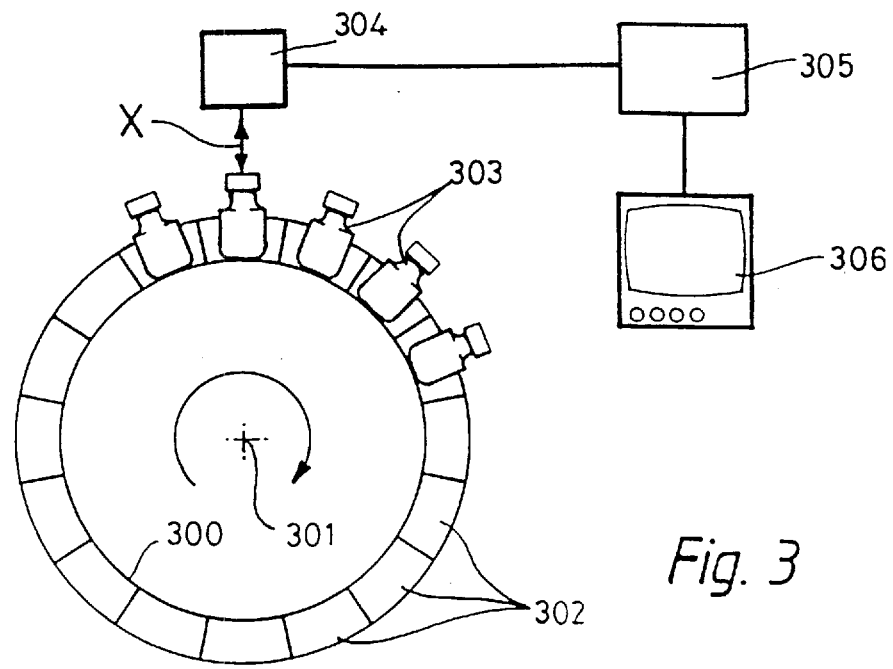
FIG. 3 is a schematic representation of one embodiment of apparatus in accordance with the invention.

FIG. 3 illustrates diagrammatically one practical arrangement of apparatus in accordance with the invention, comprising a circular carousel 300 rotatable about a horizontal axis 301, and having a plurality of identical recesses 302 around its periphery to accommodate individual culture bottles 303. A retaining means (not shown) is provided within each recess to hold the relevant bottle firmly in place when the carousel is rotated. The recesses accommodate the bottles so that the septum of each bottle is directed radially outwards from the carousel. Rotation of the carousel brings each bottle in turn beneath a laser sensor 304 which scans across the top of each bottle, and measures the distance (X) between the sensor and the centre of the septum and relates this to the distance measured between the sensor and the rim of the seal. Information from the sensor is relayed to a micro-processor 305 coupled to a visual display unit (VDU) 306 which can convey useful information about the status of each bottle to an operator of the device.

Figure 4:
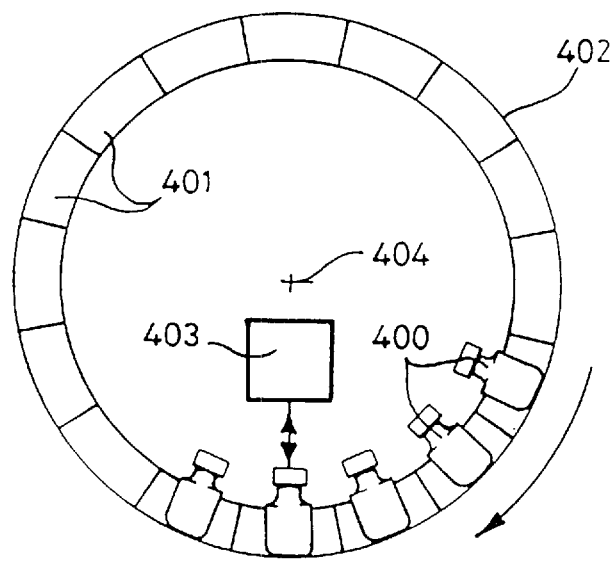
FIG. 4 is a schematic representation of a further embodiment of apparatus in accordance with the invention.

FIG. 4 illustrates an alternative arrangement wherein bottles 400 are also arranged in recesses 401 around the periphery of a carousel 402, but pointing radially inwardly instead of outwardly. A laser sensor 403 is positioned near the rotational axis 404 of the carousel. As in the FIG. 3 embodiment, the sensor 403 is linked to a microprocessor and VDU (not shown).

Figure 5:
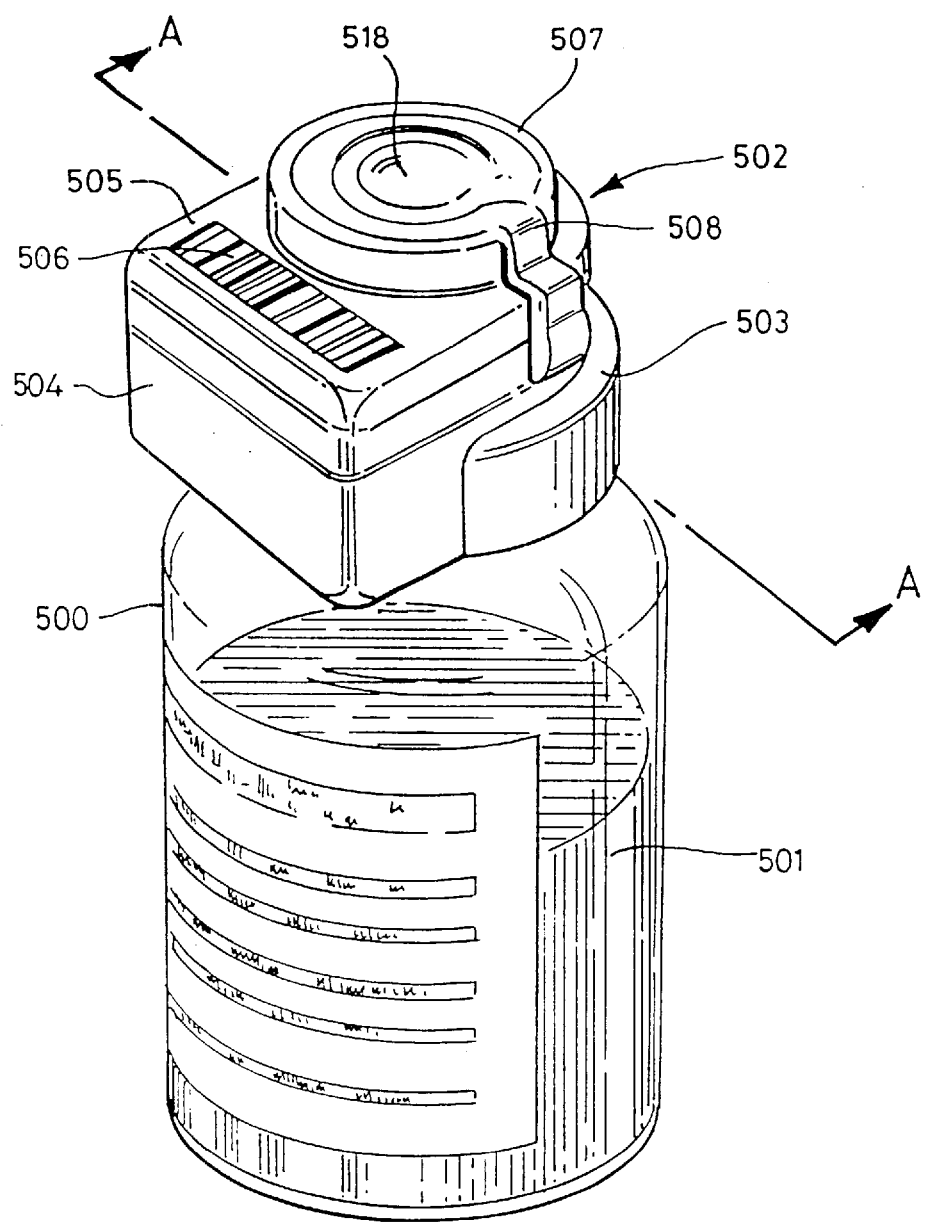
FIG. 5 is a perspective view of a culture bottle and bottle cover for use in the invention.
Figure 6:
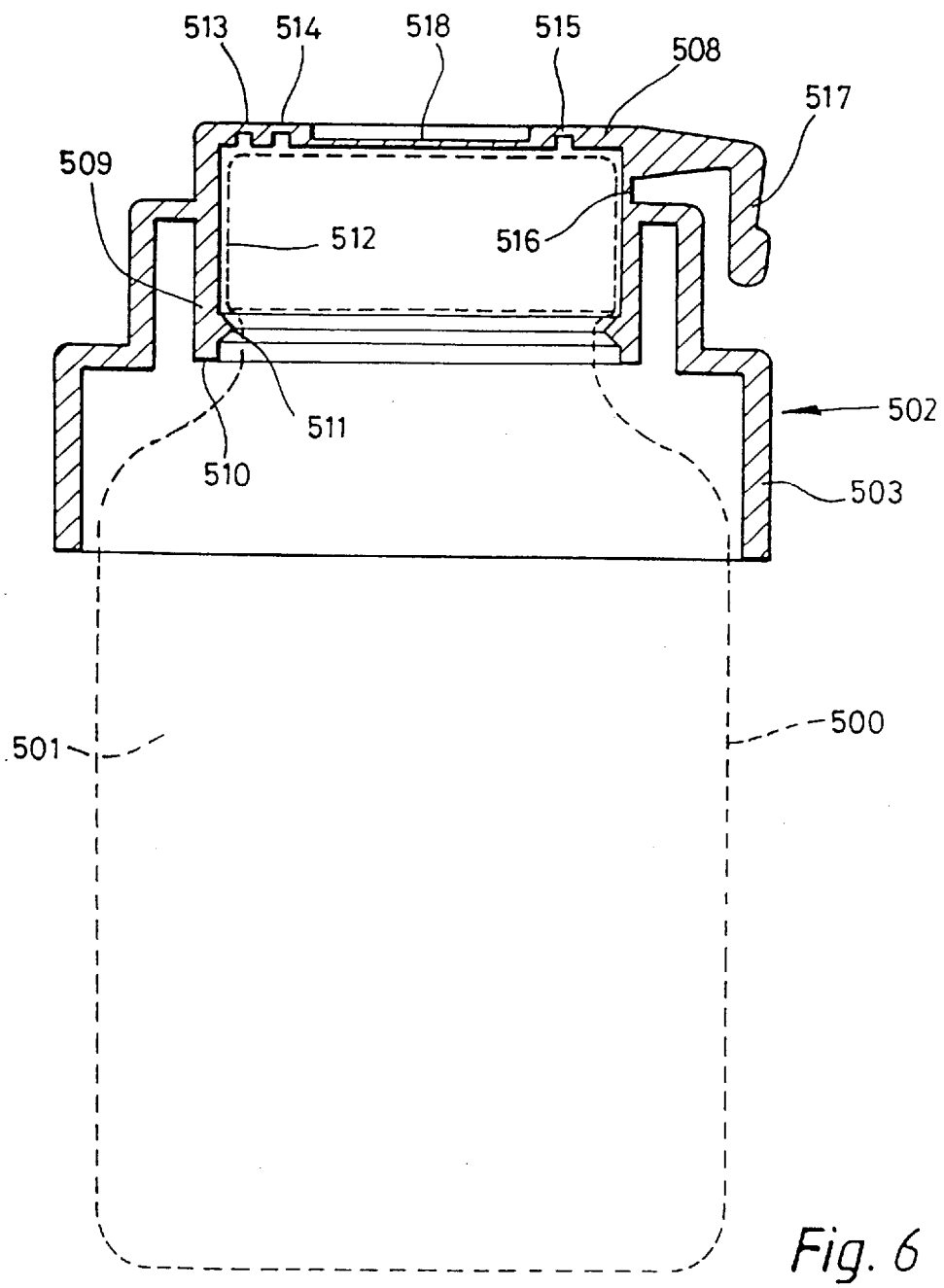
FIG. 6 is a vertical cross-section of the bottle and cover of FIG. 5 in the direction of arrows A in FIG. 5, with the bottle shown in dashed lines.

FIGS. 5 and 6 show a culture bottle 500 containing nutrient medium 501 and fitted with an over-cover 502. The over-cover comprises an essentially cylindrical body 503 shaped to conform approximately to the external configuration of the top of a standard culture bottle. A rectangular projection 504 extends from one side of body 503, and carries on a flat upper surface 505 a machine readable barcode 506. The cover includes a circular top 507, which lies over she septum (not shown) of the bottle and which incorporates a tear-off portion 508 so that the septum can be exposed without removal of the over-cover as a whole.

The cover 502 is manufactured as a single moulding, eg. from plastics material such as resilient polyethylene. As shown in FIG. 6 the over-cover 502 incorporates a downwardly extending inner sleeve 509 having at its inner lower end 510 an inwards protrusion 511 extending around the entire circumference of the sleeve which provides a snap fit when the cover is pushed over the crimped seal 512 of the standard bottle. The tear-off removable portion 508 of the cover is provided by weakened portions 513, 514, 515 and 516, and the moulding incorporates a tab 517 so that the user can effect the removal of the portion. The removable portion incorporates a central weakened portion 518 in the form of a circular thin patch which is situated directly over the septum (not shown) of the crimped cap, and therefore permits a sample to be injected by means of syringe (not shown) through the weakened portion 518 and the cap septum into the bottle. Preferably, the weakened portion 518 is in direct contact with the septum. After injection, the removable portion 508 can be torn off and discarded to expose the septum for measurement during subsequent culture of the contents of the bottle. If desired, the reference point(s) for sensing displacement of the septum can be on the cover rather that the actual bottle or bottle cap, and the cover should therefore be regarded as an integral part of the bottle when attached thereto. If desired, different cap colours can be used to signify, for example, aerobic and anaerobic media in the bottle.

Figure 7:
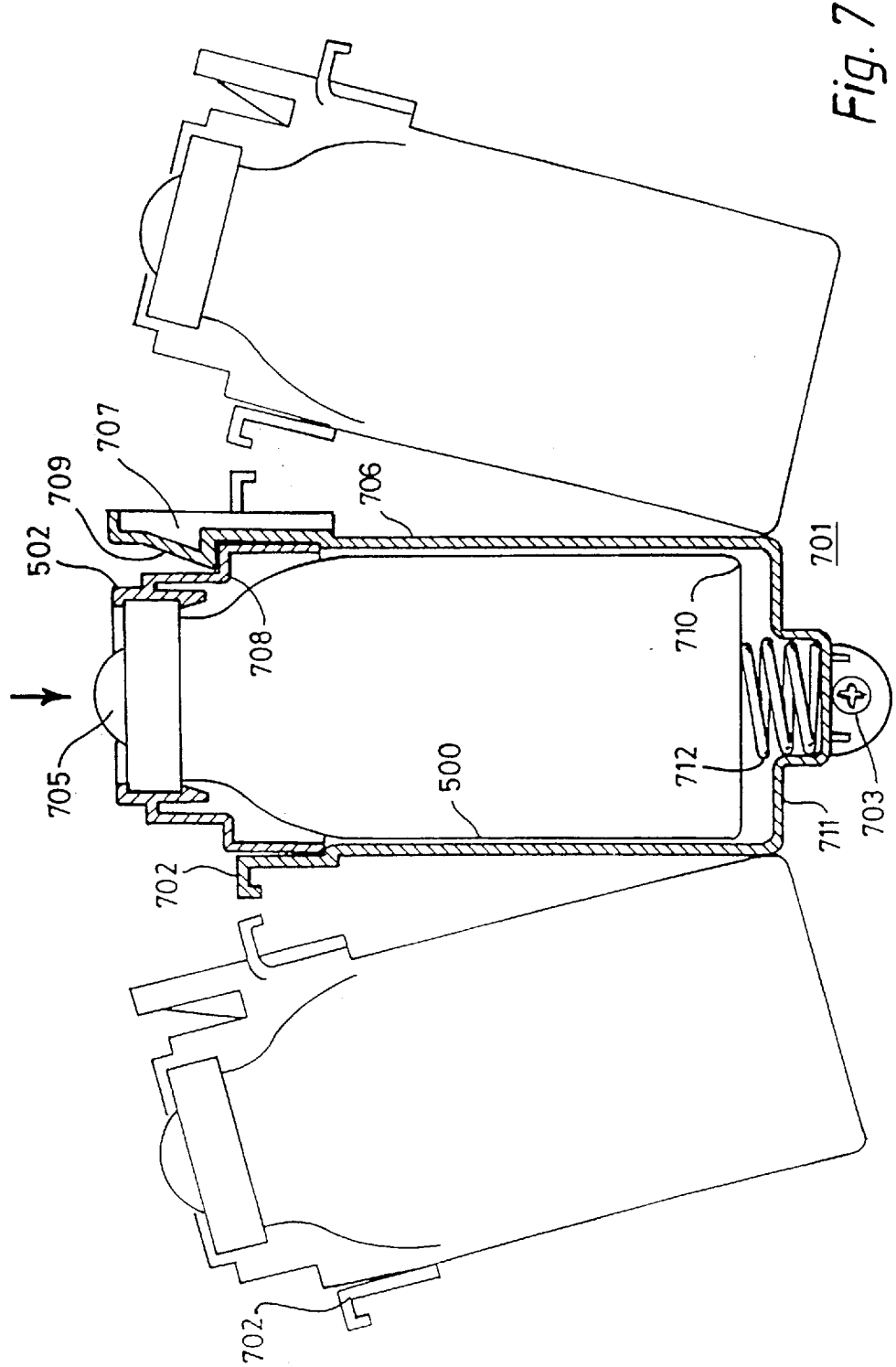
FIG. 7 is a view, partly in section, of part of a carousel arrangement of one embodiment of apparatus in accordance with the invention.

FIG. 7 shows part of the periphery of circular carousel 701. The carousel incorporates an array of recesses or "nests" 702 which can conveniently be moulded from resilient plastics material such as polypropylene. Each recess 102 is secured to the body of the carousel by respective screw means 703 and accommodates a respective single standard bottle 500 fitted with an over-cover 502 of the construction described with reference to FIGS. 5 and 6. In FIG. 7, bottle septum 705 is shown with an exaggerated outward bulge, indicating that a high pressure has developed within the bottle. At one side 706 of each recess 702 is provided a respective resilient clip 707 which can engage with a shoulder 708 on the over-cover 502 to retain the bottle within the recess. The cover (and bottle) can be released from the clip by pushing the clip sideways. The clip can conveniently be part of the recess moulding. Each clip 707 has an inwardly sloping surface 709 which contacts the base 710 during insertion of the bottle into the recess, to cause the clip to be displaced sideways. When the shoulder 708 of the cover has been pushed below the level of the clip, the clip snaps back to secure the cover (and bottle) in place. Each recess 702 is formed with a base 711 that incorporates a respective resilient compression spring 712 that can contact base 710 of a bottle and bias the bottle outwardly relative to the recess, thus maintaining the bottle securely against associated clip 707 and so reducing the risk of significant vibration of the bottle during rotation of the carousel. If desired, the recess can be adapted easily to accommodate 2 or more bottles, in a side-by-side arrangement.

Figure 8:
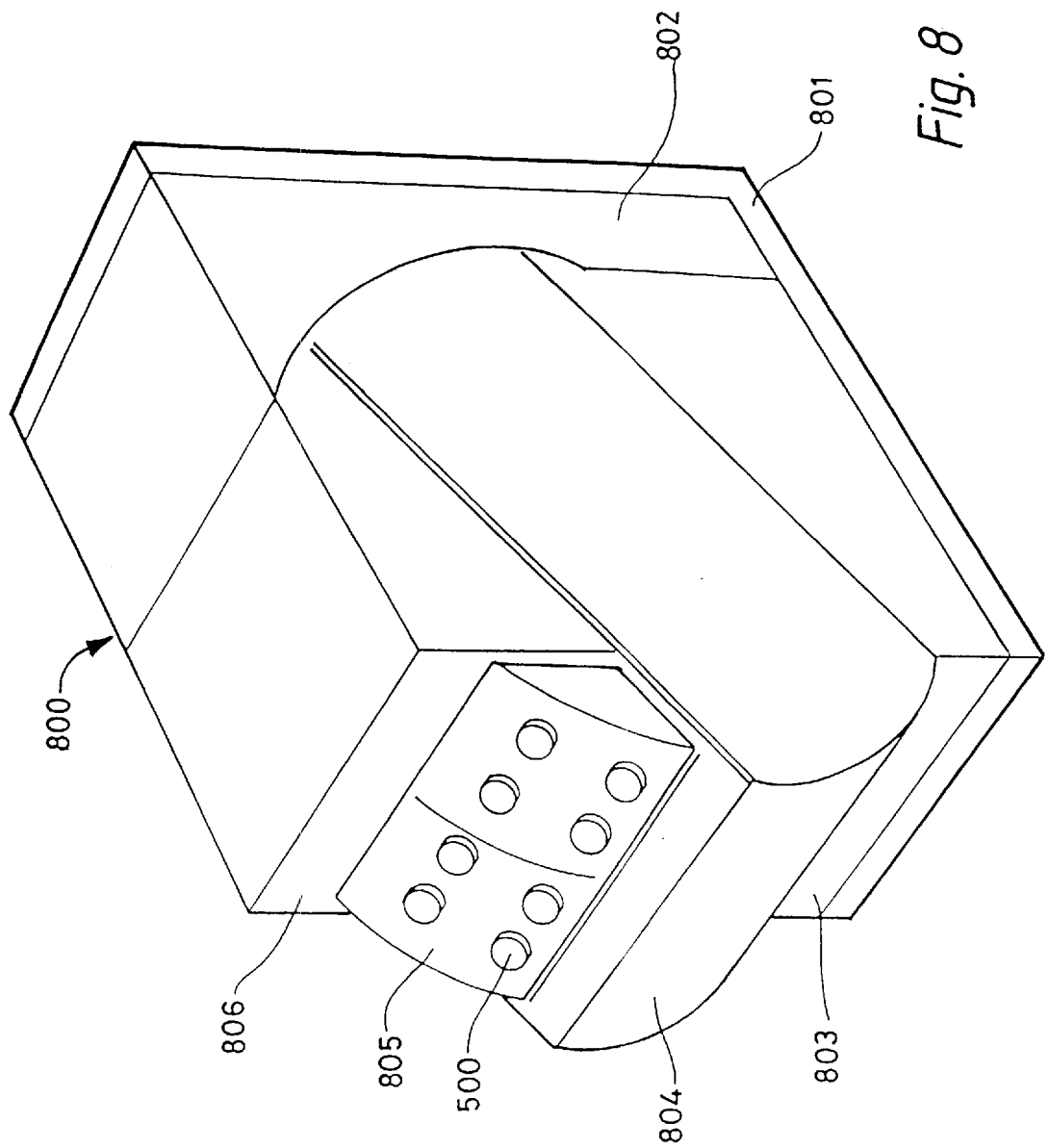
FIG. 8 is a perspective view of the exterior of a culture unit comprising apparatus in accordance was the invention.
Figure 9:
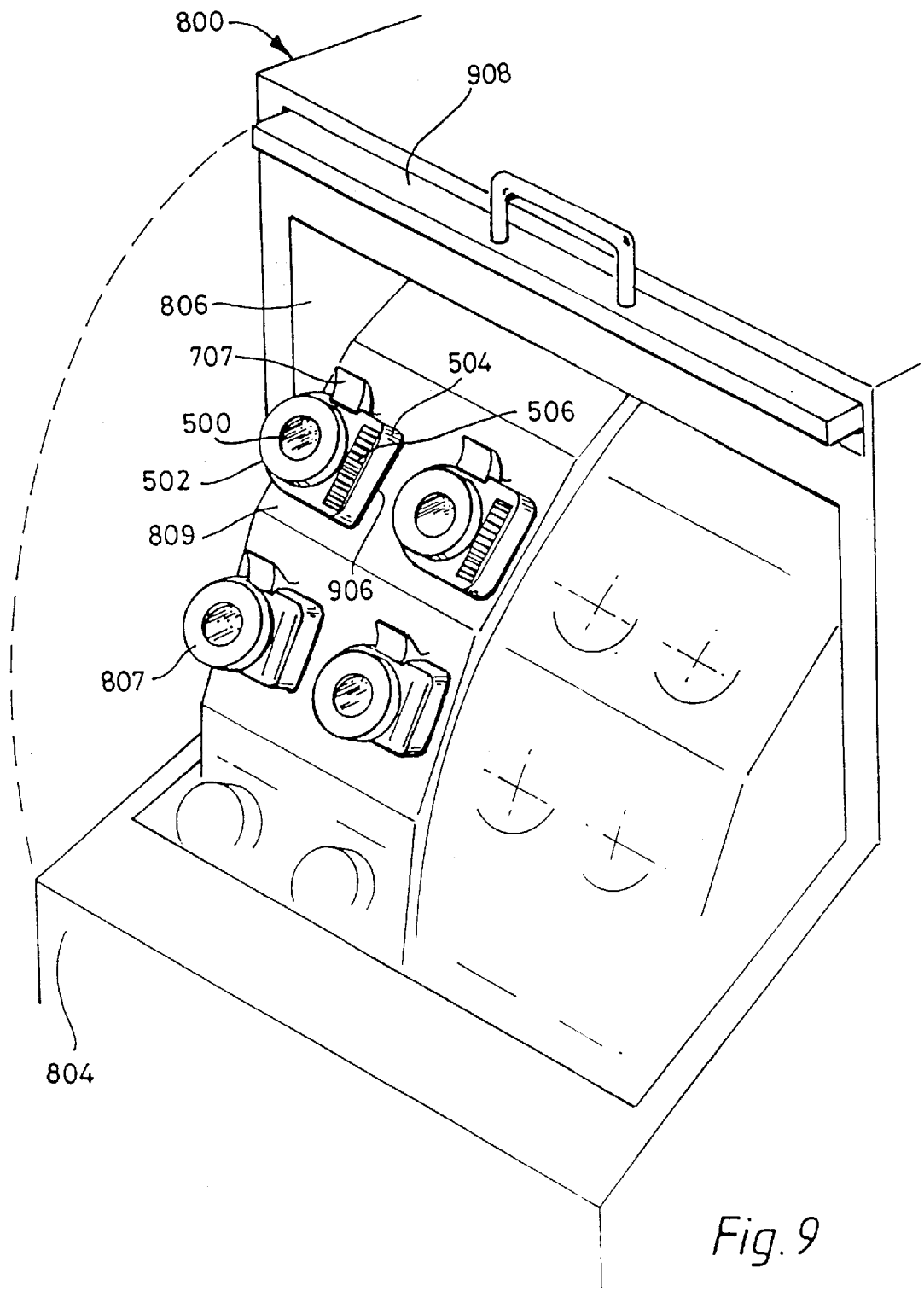
FIG. 9 is a perspective view, to an enlarged scale, of the access point of the unit or FIG. 8.

FIGS. 8 and 9 shows a culturing/sensing unit 800 incorporating the invention. The unit 800 is depicted as a floor-standing modular facility, comprising a supporting base unit 801, a rear compartment 802 to contain controlling and driving means (not shown), and a front unit 303 comprising a casing 804 for the carousel 805, and having an access point 806 at the front to enable a operator to load and unload bottles 500 into the carousel.

The unit is shown as accommodating four parallel arrays of bottles. The driving means is not critical, as long as it does not impart such vibration to the carousel and bottles that accurate sensing of septum displacement is impaired.

FIG. 9 shows an enlarged view of the access point in the unit of FIG. 8. Each bottle 500 and cover 502 is located in its individual recess 809, and retained by a spring clip 707. The rectangular projection 504 of the cover, bearing the barcode 506 on its upper surface 505, is located in a correspondingly shaped recess 906 in the top of the recess. The barcode is therefore presented in a constant position relative to each bottle, and can pass under a barcode reader while the carousel is rotated.

The laser sensing means of the diaphragm and the barcode reader (which may be a combined unit), are not seen as these are enclosed within the casing 806 of the unit.

The access point has a openable and closable cover 908 that can be opened and closed by being slid up and down, manually or automatically, when is is necessary to load or unload bottles into the unit. Closure of the cover facilitates maintenance of a constant incubation temperature within the unit.

The unit is also provided with control means and information display or result printout means (not shown) to provide the operator with information on the status of each bottle in the unit. The unit also incorporates heating means (not shown) to enable a constant temperature appropriate for incubation to be maintained within the unit. Desirably, the control means will incorporate facilities to enable the operator to start and stop the rotation of the carousel at will, and also to provide indications to the operator that the carousel should be stopped and particular bottles removed if for example positive results have already been obtained from a bottle in the device. In particular, it will be useful if the operator is given warning that incubation of a particular bottle has proceeded to such a degree that a dangerously high pressure is building up in the bottle.

FIGS. 10 to 13 illustrate an alternative embodiment of the invention, comprising a stationary flat bed in which a plurality of bottles are located, and a movable laser arranged repeatedly to scan the bottles in turn.

Figure 10:
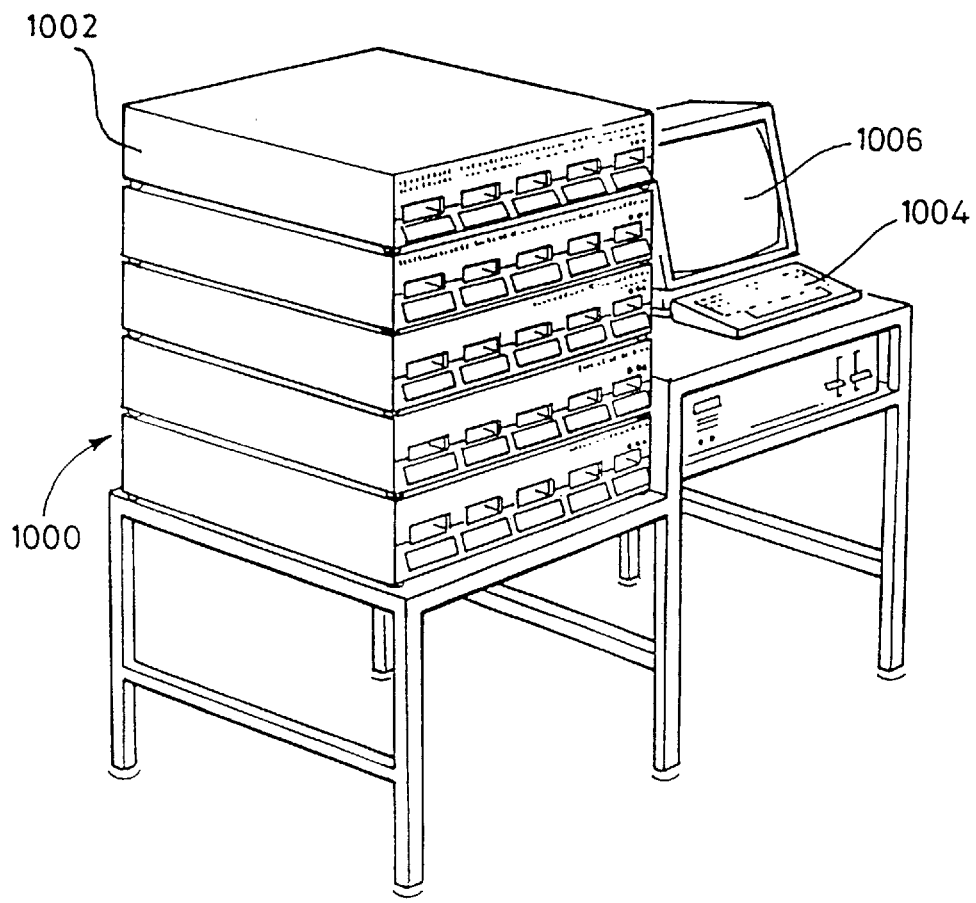
FIG. 10 is a diagrammatic perspective view so an automated culture unit comprising a further embodiment of apparatus in accordance withe the invention.

The embodiment is illustrated generally in FIG. 10, and comprises a unit 1000 removably housing 5 similar drawers 1002 for receiving bottles, and also computer control means 1004 with an associated visual display unit 1006.

Figure 11:
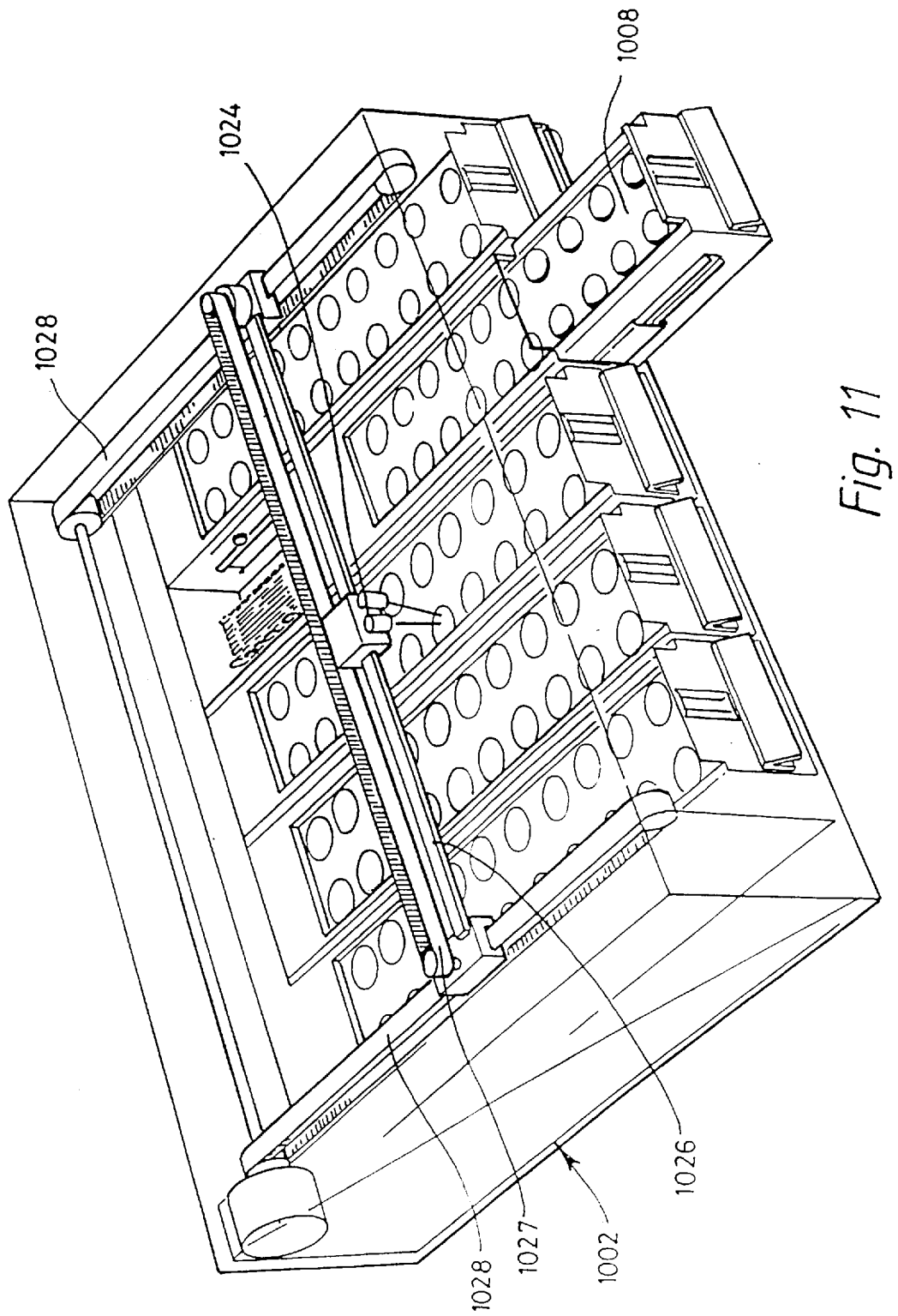
FIG. 11 is a perspective view of part of the unit of FIG. 10, shown to an enlarged scale.

As shown in FIG. 11, each drawer 1002 comprises 5 similar supports 1008, each slidably received therein and independently removable therefrom is shown in FIGS. 11, 12 and 13, each support 1008 comprises two apertured aluminium blocks 1009, defining two side by side rows of 10 similar recesses 1010, each for receiving a respective sample bottle (not shown), eg of the construction described above, so that the bottle is fully received within the recess for good temperature regulation.

A respective magnetic stirrer drive 1012 (FIG. 13) is locates beneath each recess and comprises two neodymium-boron magnets 1014 fixedly mounted in a rotatable support 1016 with opposed polarity. As shown in FIG. 12, a drive motor 1018 is located in each support 1008 and is arranged to drive a drive belt 1020 passing around the drives 1012 associated with both rows of recesses in the support, with the drive belt preferably passing around adjacent pairs of drives in a serpentine drive arrangement rather than the alternating arrangement illustrated.

As shown in FIG. 13, each support 1008 also includes a heating block 1022 in the form of a rubberised electrically heatable element clamped between the aluminium blocks 1009. Each support 1008 also includes a repsective printed circuit board 1024 for controlling the associated drive motor 1018 and heating block 1022.

A sensor (not shown) comprising a Hall effect transistor is located in the vicinity of one drive 1012 in each support 1008 to sense appropriate movement of the associated drive and hence indicate to the computer control means correct functioning or otherwise of the magnetic stirrer drives of that support.

Referring to FIG. 11, each drawer 1002 further comprises a laser 1024 (eg. a Matsushita LA40 laser) mounted for movement in two perpendicular directions (X and Y) on a generally conventional X—Y motion controller. The controller comprises a cross-rail 1026 on which laser 1024 is mounted for sliding movement in an X direction under the action of a stepper-motor driven belt drive 1027. The ends of rail 1024 are carried by stepper-motor driven belt drives 1028, for causing movement in a Y direction.

In use, sample containing bottles are loaded into recesses 1010, with each bottle containing a respective disposable magnetic stirring device, conveniently in the form of a sintered ferrite magnet 20 mm in length and 6 mm in diameter. The drive motor 1018 for each support 1008 in use is activated, causing stirring of the bottle contents by rotation of the disposable magnets within the bottles. A drive speed of at least 200 rpm, typically about 220 rpm, is found suitable. The heating element 1322 of each support in use is activated to produce heating to a desired temperature, typically about 37° C.

Under control of the computer control means, the laser 1024 of each drawer in use then performs a checking routine to check whether there is a bottle in each recess in that drawer; if not, the control means will calculate the most efficient sequence for checking all the bottles present in turn.

In normal use, the laser performs a scanning cycle once every five minutes. Scanning a full drawer (containing 100 bottles) takes about 2½ minutes, and scanning a partially full drawer will take a shorter time. This is followed by a rest period of 2½ minutes for a full drawer or more for a partially full drawer. The results of each scan of each bottle are conveyed to the computer control means for suitable processing and display on the VDU if appropriate. When a positive result is detected for a particular bottle, this information is made available to an operator, eg by a suitable message on the VDU. The bottle can then be removed from the apparatus.

As a safety feature, the laser 1024 may carry a sterile venting needle (not shown) that is used to puncture the septum of a bottle sensed as having developed an excessive outward bulge indicative of a dangerous build up of gas within the container.

EXAMPLES

Experimental Method

Appropriate media—see below—were sterilised in 90 ml amounts in standard round DIN bottles with crimped septum cap and cover in place, as described above with reference to FIGS. 5 and 6.

For use, the septum was exposed by removing the cover tear-off portion, and a blood sample and an experimeental inoculum of bacteria injected through the sterile septum using a syringe. Head space volume after addition of blood was about 25 ml—this is not critical and will vary with blood volume added in the typical clinical situation. Controls of bottles of media+blood sample (no bacteria) were also prepared.

Bottles were placed into holders on a circular 660 mm diameter carousel. Bottles were positioned on the outside edge of the carousel with septum pointed inwards, and the laser sensor (Matsushita LA 40) positioned at the centre of the carousel with the sensing head about 50 mm from septa in the reading position. The carousel was rotated at about 3 revs/minute.

The laser sensor was positioned to read diametrically opposed points on the side of the cap as reference points, and across the septum. The sensor was linked to a computer, which recorded data and calculated change in the highest point of septum, and change in height with time (readings are made every 4 minutes); these changes were logged and further calculations made ie. smoothing of data and rate of change.

The unit was housed in a temperature-controlled environment. There was a 3-hour warm-up time to 37° C., during which gas expanded in the bottle head space and gave a steeply rising graph; then readings became constant prior to bacterial growth at detectable levels. The atmospheric pressure is also monitored, and the computer software adjusted results to take into account any variations in atmospheric pressure.

Data was studied for sharp changes in septum position (positive or negative) indicating bacterial growth. Detection of a sufficiently large rate of change is indicative of bacterial growth, providing a positive result, and the time at which this is detected is called the detection time. Positive bottles were checked for purity by sub-culture to appropriate standard bacteriological media.

Figure 14:
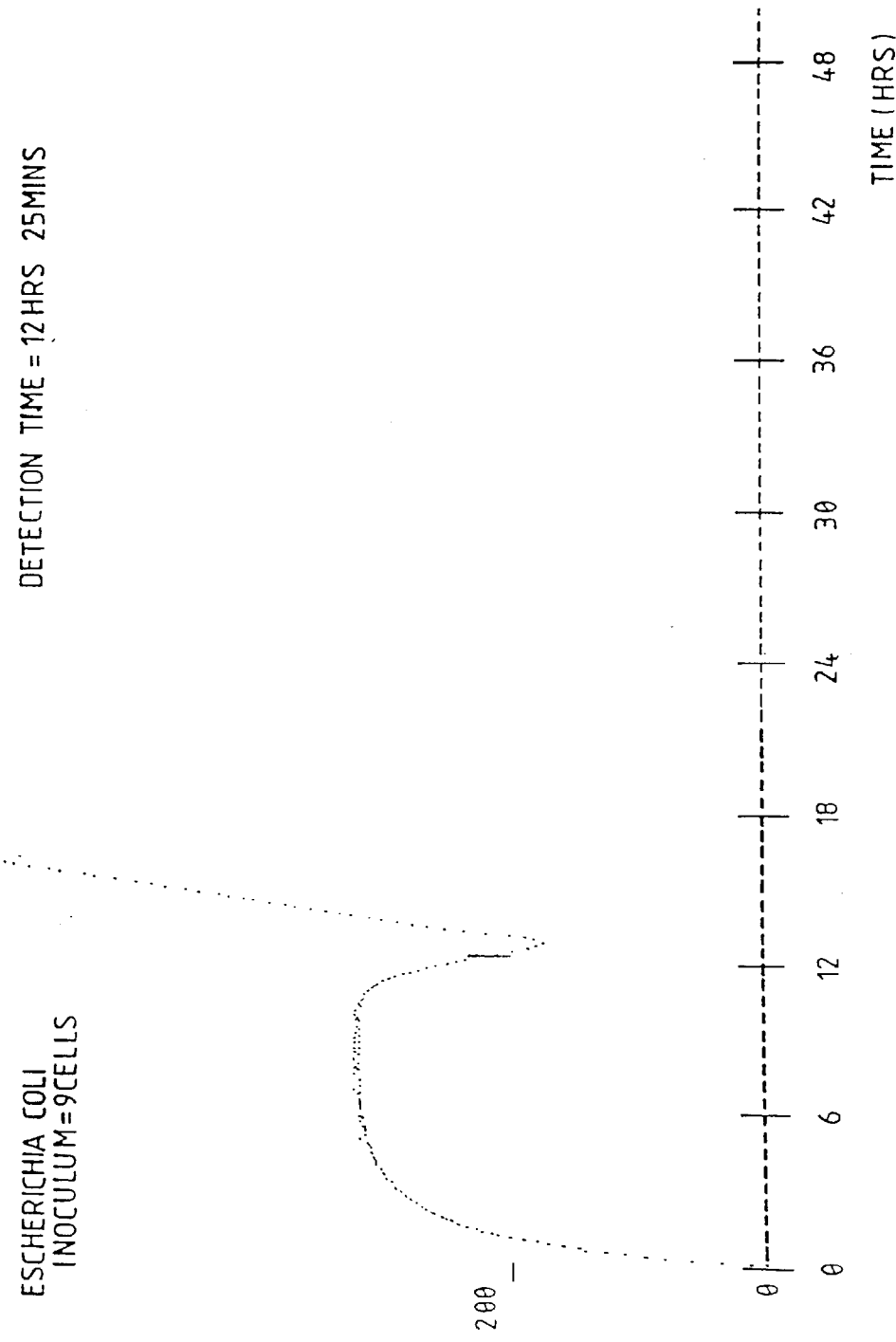
FIGS. 14 to 16 are each plots of septum position against time obtained in a series of culture experiments with different micro-organisms using an apparatus according to the invention.
Figure 15:
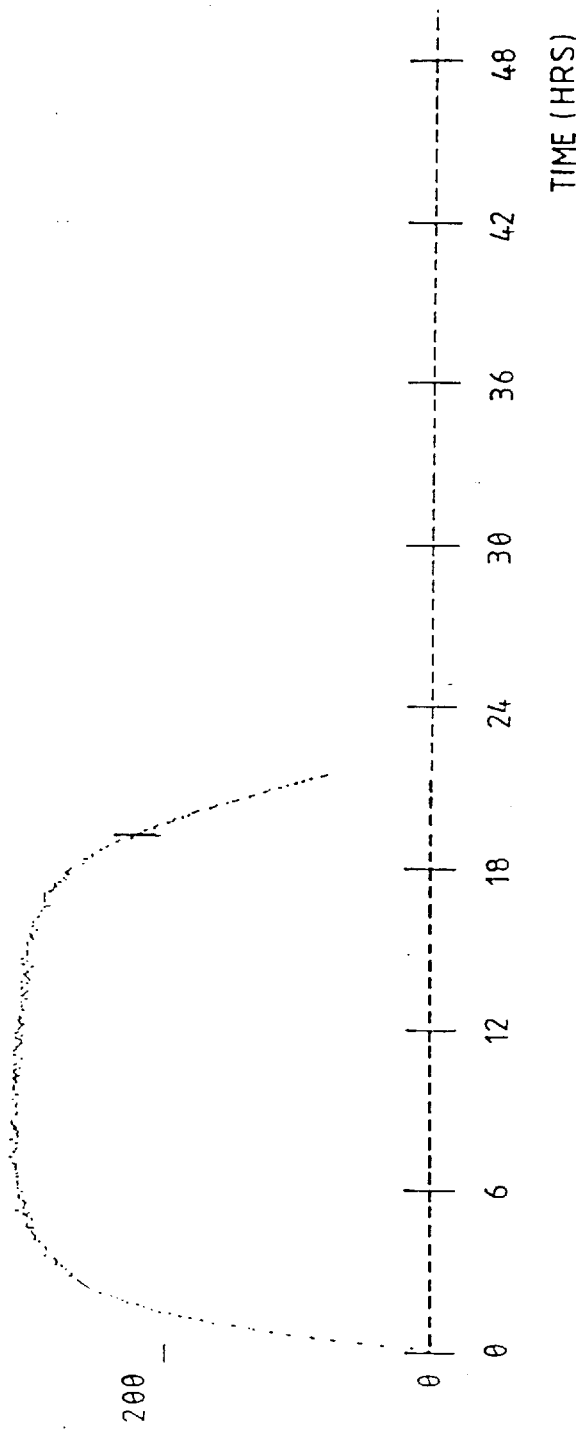
Figure 16:
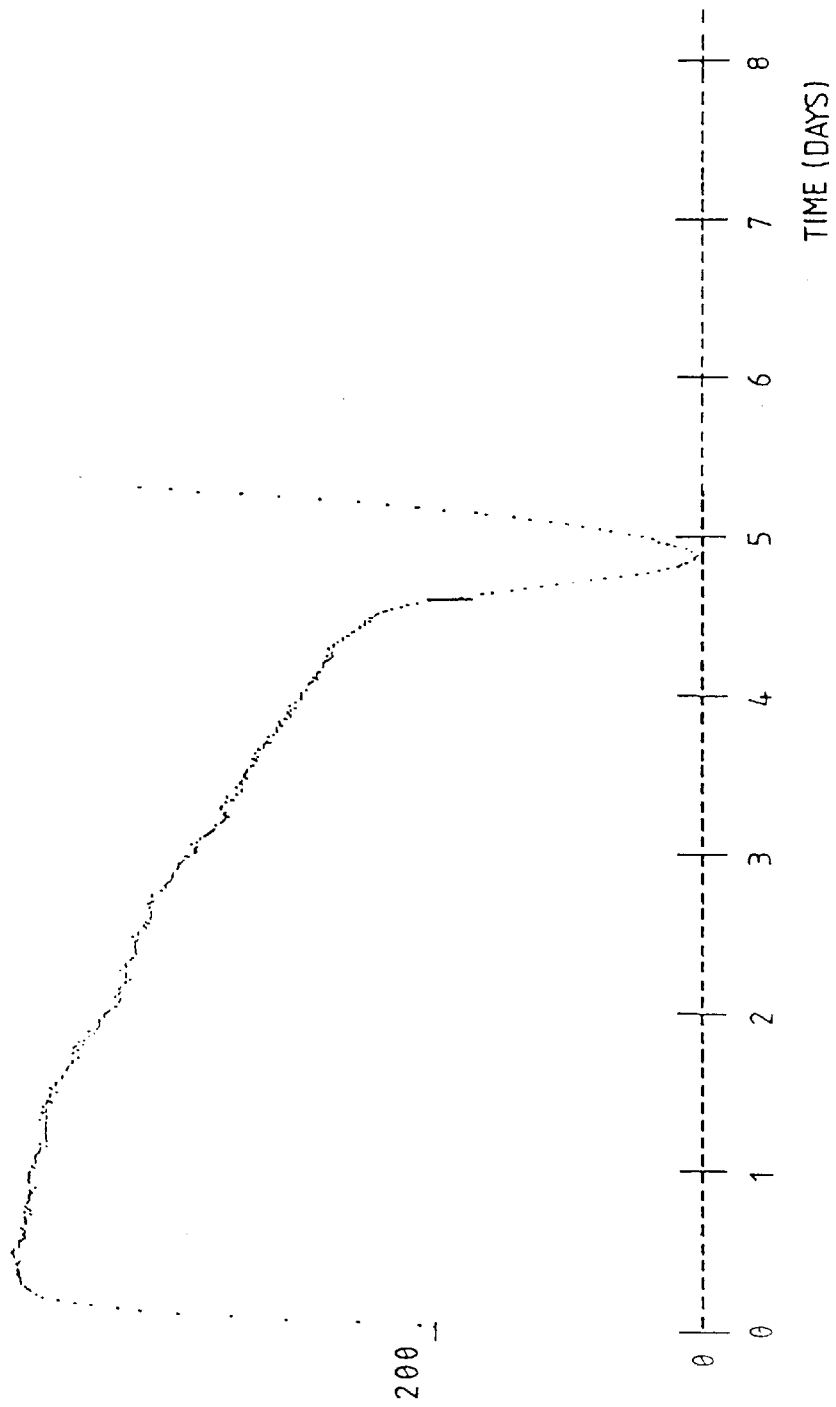

FIGS. 14 to 16 are graphs showing septum displacement (in arbitrary units) against time, for three bottles containing three different bacteria.

Bacteria Used and Results

Results are given from experiments with three common bacteria; 2 aerobes, *E.coli* and *Pseudomonas aeruginosa*, and 1 anaerobe *Peptostreptococcus anaerobius*.

Events as recorded so the computer are given in FIGS. 14–16 with organisms listed in Table 1. For comparison purposes, detection time for these organisms using a commerically-available detection system (Bactec 460 from Becton Dickinson) is also given in the Table. All graphs show an initial increase in pressure due to gas expansion as the bottles warm up to incubation temperature, with subsequent behaviour varying with the type of organism. The detection time is indicated on the graphs by a short vertical line.

Media Formulations

For aerobes:

Commercially-available Oxoid "Tryptone Soya Broth CM 129".

|  | g/liter |
|---|---|
| Pancreatic digest of casein | 17.0 |
| Papaic digest of soybean meal | 3.0 |
| Dibasic potassium phosphate | 2.5 |
| Glucose | 2.5 | pH 7.3±0.2

For anaerobes:

Oxoid "CM 129", with the addition of filter-sterilised solutions of:

| 0.02% Resazurin | 0.5 ml |
| 1% Dithiothreitol | to render the medium anaerobic. |

TABLE 1

| Strain | Inoculum level (cells) | Detection Time (hours) Invention | "Bactec 460"* |
|---|---|---|---|
| Escherichia coli | 9 | 12.4 (FIG. 14) | 17.0 |
| Pseudomonas aeruginosa | 6 | 19.2 (FIG. 15) | 24.0 |
| Peptostreptococcus anaerobius | 2800 | 110.2 (FIG. 16) | 168.0 |

*Commercially-available detection system, from Becton-Dickinson.

We claim:

1. In a method of monitoring the growth of microorganisms in liquid culture in a gas-tight container incorporating a flexible diaphragm capable of moving in response to pressure changes within the container, by detecting displacement of the diaphragm, the improvement wherein the position or conformation of the diaphragm is repeatedly sensed using a laser as distance-measuring means, and wherein a portion of the container adjacent the diaphragm is used as a reference against which all relative positional or conformational changes of the diaphragm are detected, said diaphragm being capable of moving between concave and convex configurations in response to pressure changes within the container.

2. A method according to claim 1, where the distance-measuring means are capable of detecting variation in the position or conformation of the diaphragm to an accuracy of at least 200$\mu$.

3. A method according to claim 1, wherein the distance-measuring means repeatedly scans a plurality of containers.

4. A method according to claim 3, wherein the plurality of containers are arranged in an array with the array and distance-measuring means arranged for relative movement such that the containers are sequentially scanned by the distance-measuring means.

5. A method according to claim 4, wherein the containers are mounted in a carousel which can revolve continuously about a horizontal axis, and the plurality of containers are arranged around the circumference of the carousel such that rotation of the carousel generates end-over mixing of the contents of the containers.

6. A method according to claim 4, wherein the containers are located in a generally stationary holder and the distance-measuring means moves with respect thereto to scan the containers in turn.

7. A method according to claim 6, wherein the contents of the containers are stirred by means of a respective magnetic stirrer in each container.

8. A method according to claim 7, wherein each container displays a unique machine-readable identifying reference.

9. A method according to claim 8, applied to the monitoring of blood samples.

10. The method of claim 8 wherein the machine-readable identifying reference is a bar-code.

11. A method according to claim 1, wherein the barometric pressure adjacent the container is sensed, and the sensed position or configuration of the diaphragm is adjusted to account for variations in the sensed barometric pressure.

12. Apparatus for monitoring the growth of microorganisms in liquid culture, comprising means for holding an array of gas-tight containers each containing a liquid test sample and each incorporating a flexible diaphragm capable of moving in response to pressure changes within the container, distance measuring means, in the form of a laser, capable of detecting changes in position or conformation of each diaphragm, said laser being arranged with respect to the container such that a portion of the container adjacent the diaphragm is used as a reference against which all relative positional or conformational changes of the diaphragm are detected, said diaphragm being capable of moving between concave and convex configurations in response to pressure changes within the container, means for providing relative movement between the containers and the distance-measuring means for repeatedly presenting the containers individually in turn to the distance-measuring means, and means for recording and/or displaying data obtained from the distance measuring means.

13. Apparatus according to claim 12 wherein each gas-tight container comprises a septum-sealed culture bottle including a cover, said cover incorporating locating means that enable the bottle and the cover to be positively located in the container holding means.

14. An apparatus according to claim 13, wherein said cover incorporates a tear-off sealing portion protecting a septum.

* * * * *